United States Patent [19]

Hansjürgens et al.

[11] Patent Number: 4,598,713
[45] Date of Patent: Jul. 8, 1986

[54] ELECTROSTIMULATION THERAPY DEVICE AND METHOD

[75] Inventors: Achim Hansjürgens; Gerhard Mionskowski, both of Karlsruhe, Fed. Rep. of Germany

[73] Assignee: Deutsche Nemectron GmbH, Karlsruhe, Fed. Rep. of Germany

[21] Appl. No.: 708,503

[22] Filed: Mar. 5, 1985

Related U.S. Application Data

[63] Continuation-in-part of Ser. No. 393,337, Jun. 29, 1982, abandoned.

[51] Int. Cl.⁴ ............................................. A61N 1/36
[52] U.S. Cl. .................................. 128/421; 128/422; 364/413
[58] Field of Search .................. 128/419 PG, 421–422; 364/413, 487

[56] References Cited

U.S. PATENT DOCUMENTS

| | | | |
|---|---|---|---|
| 4,049,004 | 9/1977 | Walters | 128/419 PG |
| 4,071,033 | 1/1978 | Nawracaj et al. | 128/422 |
| 4,192,316 | 3/1980 | Walters et al. | 128/419 PG |
| 4,254,776 | 3/1981 | Tanie et al. | 128/421 |
| 4,255,790 | 3/1981 | Hondeghem | 364/413 |
| 4,323,074 | 4/1982 | Nelms | 128/419 PG |
| 4,338,945 | 6/1982 | Kosugi et al. | 128/421 |
| 4,390,022 | 6/1983 | Calfee et al. | 128/419 PG |
| 4,390,023 | 6/1983 | Rise | 128/421 |
| 4,404,972 | 9/1983 | Gordon et al. | 128/419 PG |
| 4,455,613 | 6/1984 | Shoemaker | 364/487 |
| 4,540,938 | 9/1985 | Bruce | 364/487 |

Primary Examiner—William E. Kamm
Assistant Examiner—Mitchell J. Shein
Attorney, Agent, or Firm—Sandler & Greenblum

[57] ABSTRACT

A device for the electrostimulation therapy of a type having at least one circuit with a pair of electrodes, a program memory and a control unit is provided with a microprocessor for producing desired curves and frequencies responsive to information and instructions from program memory and the control unit, an intermediate memory associated with the microprocessor for storing data in the form of instantaneous values representing the curves and frequencies, and address means for providing an output of the instantaneous values stored in the intermediate memory responsive to a demand from the microprocessor for information for providing a curve. The device can be adapted for electrical interference therapy such that the device has two separate circuits and two associated pair of electrodes. The adapted device has an intermediate memory, for storing instantaneous values, connected with each of the separate circuits. Means for varying the shape of the output curves and also means for varying the period of one of the output curves are provided. A method for providing signals of variable shapes at the output of an electrostimulation therapy device is also disclosed.

26 Claims, 4 Drawing Figures

ELECTROSTIMULATION THERAPY DEVICE AND METHOD

CROSS-REFERENCE TO RELATED APPLICATIONS

This application is a continuation-in-part of U.S. Ser. No. 393,337 filed June 29, 1982, now abandoned.

BACKGROUND OF THE INVENTION

1. Field of the Invention

The invention relates to a device for electrostimulation therapy with at least one circuit with a pair of electrodes, at least one amplifier, an impulse oscillator, a program memory and an input unit as well as a control unit.

2. Description of the Prior Art

Devices of this type for electrostimulation therapy, and particularly for electrical interference therapy, in other words, a therapy by which medium frequency voltages with frequencies in the range of a few thousand Hz are applied over at least two circuits each with one pair of electrodes, which differ from each other by a low frequency range of from a few to a few hundred Hz, so that stimulations, and thereby therapeutically effective oscillations called beats, occur with correspondingly low frequency in the body, are known. Devices of this type work basically satisfactorily and have a remarkable effectiveness and success of treatment.

Problems of the medium frequency voltages with known analogous devices, in that the frequency difference giving the beat frequency - caused by interference of the medium frequencies - signals particularly if quite small, cannot be held sufficiently stable, since it is influenced by outside factors, such as temperature, feed voltage, humidity, aging of material and scatter values of the modular components.

With the development of electronic digital technology, the problem of stability has been solved in large measure by digitization. Sufficient stability of the beat frequency can be attained digitally. In digital technology, however, low beat frequencies can be produced only with very extensive technical and financial outlay. A high-frequency, quartz-controlled oscillator is used for this purpose, of which the frequency is divided down in two different ways, i.e., by two different divider ratios by means of digital elements. The smaller the desired frequency difference of the medium frequency oscillations, the higher the oscillator frequency and the larger and more expensive the outlay will be for dividing down the frequency and for producing small frequency differences of the medium frequency output oscillations.

This problem arises particularly when a dense frequency spectrum must be made available for the treatment, i.e., on the one hand, when various closely-spaced beat frequencies must be supplied, and, on the other hand, when the treatment requires that this frequency spectrum be run through quasicontinuously or possibly periodically, i.e., for example, between 5 and 20 Hz in a time period of 10 to 15 seconds. The high resolution required for this, i.e., the spacing between two adjacent beat frequencies, (e.g. 10 Hz and 10.1 Hz) to be run through in succession, can be attained in digital technology only at very high cost. For example, with two current circuits with medium frequency each in the range of ca. 4 thousand Hz and a desired resolution—i.e., the lowest frequency spacing between the two medium frequencies or the smallest "step" for changing the beat frequency—of one must operate with a pulse frequency of 160 MHz. The use of a pulse oscillator and frequency divider with such a high frequency is neither technically nor commercially justifiable in mass production of electrical interference devices.

Another problem is that, in the devices described above, with reasonable technical outlay, it is not possible to attain of various curve shapes, both the medium frequency output signals and the beats.

In order to solve the last problem with known devices of this type, the procedure is to store the various curves of medium frequency output signals in the usual known memory devices and to call them as needed. Such storage can be effected by analog means or, with the development of digital technology, and especially digital memories, by digital processes; the respective cited specific problems and drawbacks remaining the same in either case. This storage can be accomplished, for example, by means of disks, tape memories, core memories, using magnetic record technology or the usual solid state memory devices, such as large-scale integration (LSI) semiconductor memories, including ROM's i.e., Read Only Memories, PROE's, i.e., Programmable Read Only Memories, or even EPROE's, i.e., Erasable and Programmable Read Only Memories in an appropriate known manner. Reading can be accomplished by equally familiar addressing techniques, for example, directly from the keyboard to use a method a long known in the art. This approach is disadvantageous, in addition particularly to the already cited analog- or digital-specific problem, in that a very high memory outlay is needed for the required processing. Also, with inexpensive memories, such as tapes, the danger exists that the signal cannot be retrieved over a long time (years) with the same good and therapeutically necessary quality. Also, undesirable frequency fluatuation arise because of defective synchronization of tapes.

SUMMARY OF THE INVENTION

Therefore, the object of the invention is to improve upon known devices of the aforementioned type, such that the most varied output curves can be produced with justifiable technical outlay, particularly with use of electrical interference therapy, and such that both the medium frequency output signals and the interference beats produced can have sufficient stability of frequency and sufficiently high resolution, thus making possible small spacing of adjacent frequencies.

According to the invention, this object of the invention there can be implemented by a device for electrostimulation therapy for producing an output signal having a desired sequence of instantaneous value changes and in a desired wave shape and frequency to stimulate a portion of the human body. By instantaneous values are particularly understood the instantaneous voltage values determining the time-dependent course of the voltage curve. The device comprises a program memory, an adjustable control unit, an intermediate memory, a microprocessor, a digital-to-analog converter, at least one electrode, and an address means. The program memory stores data comprising of plurality of discrete different values representative of signals having predetermined instantaneous value variations with time. Each discrete value comprises a particular instantaneous value of the signal at a particular time. The adjustable control unit selects a desired sequence of instantaneous value changes and a desired wave shape and a desired frequency of the output signal. The intermediate memory receives and stores data from the program memory. The microprocessor is responsive to the control unit and selects data in a predetermined sequence from the program memory so as to produce a plurality of discrete values in a predetermined sequence corresponding to the desired sequence of the instantaneous value changes. The microprocessor also transfers these discrete values to the intermediate memory in the predetermined sequence. At least one electrode is connected to the output of the digital-to-analog converter for engaging the exterior of the body. The output signal of the device is transferred to the body through at least one electrode. The address means is responsive to the microprocessor and transfers the discrete values stored in the intermediate memory to the digital-to-analog converter in this predetermined sequence and at a predetermined speed so as to produce an output signal having the desired sequence of instantaneous value changes and the desired wave shape and frequency selected by the adjustable control unit.

The device can further comprise a pair of electrodes connected to the converter for engaging the exterior of the body and an amplifier for amplifying the output signal before the output signal reaches the pair of electrodes. In addition, an oscillator can be provided for controlling the speed with which the address means transfers the discrete values from the intermediate memory to the digital-to-analog converter. A frequency divider can also be provided, and the address means can further comprise a chronological address allocation unit. In this embodiment, the oscillator is connected to the frequency divider so that this chronological address allocation unit is controlled by the oscillator and the frequency divider. The chronological address allocation unit can further comprise memory means for storing a function relating to the varing of the wave shape of the output signal, so that the chronological address allocation means varies the wave shape of the output signal in accordance with the function stored in the memory means. In one embodiment, this function is a non-linear function so that the chronological address allocation unit varies the wave shape of the output signal in a non-linear manner in accordance with this non-linear function. In one embodiment, this memory means may be a programmable memory and the chronological address allocation unit can comprise at least one counter controlled by the oscillator.

In still another embodiment, the device is adapted to produce first and second output signals, each having a desired wave shape, frequency and sequence of instantaneous value changes. In this embodiment, the device further comprises a first and second electrode and first and second digital-to-analog converters. The first electrode is connected to the output of the first digital-to-analog converter and the second electrode is connected to the output of the second digital-to-analog converter. Each electrode engages the exterior of the body so that the first output signal is transmitted to the body through the first electrode and the second output signal is transmitted to the body through the second electrode. In this embodiment, the intermediate memory comprises a first intermediate memory for receiving and storing date from the program memory, and a second intermediate memory for receiving and storing data from the program memory. The control unit selects a desired sequence of instantaneous value changes and a desired wave shape and frequency for each output signal. Also, the microprocessor selects discrete values in a predetermined sequence from the program memory so as to produce a first set of data comprising a plurality of discrete values in a predetermined sequence corresponding to the desired sequence of instantaneous value changes for the first output signal. In addition, the microprocessor selects discrete values in a predetermined sequence from the program memory so as to produce the second set of data comprising a plurality of discrete values in a predetermined sequence corresponding to the desired sequence of instantaneous value changes for the second output signal. In addition, the microprocessor transfers this first set of data in this predetermined sequence to the first intermediate memory and the microprocessor transfers the second set of data in this predetermined sequence to the second intermediate memory. The address means transfers the first set of data from the first intermediate memory to the first digital-to-analog converter and transfers the second set of data from the second intermediate memory to the second digital-to-analog converter, whereby the device comprises means for performing electrical interference therapy on the body. The address means can transfer the first and second sets of data from the first and second intermediate memories in such a manner so as to maintain the predetermined sequence of discrete values in the first and second intermediate memories, or the address means can change this predetermined sequence of discrete values in each intermediate memory as these discrete values are transferred out of each intermediate memory.

The address means can further comprises means for transferring the first set of data from the first intermediate memory at a first speed to produce a first output signal. In addition, the address means can further comprises means for transferring the second of data from the second intermediate memory at a second speed to produce the second output signal so that the frequency of the first output signal is different from the frequency of the second output signal. In addition, the frequency of the two output signals produced by the address means are sufficiently close together that beats are produced when the adder adds the two output signals together.

The device can further comprise an additional memory for storing instructions for the sequence in which the discrete values are transferred from the second intermediate memory by the address means and for the frequency of the second output signal produced from the discrete values in the second intermediate memory by the address means. This address means transfers the second set of data out of the second intermediate memory in accordance with the instructions in the additional memory.

In addition, the address means can change the sequence of discrete values in the second set of data stored in the second intermediate memory as the address means transfers the second set of data out of the second intermediate memory in accordance with instructions stored in the additional memory. In this manner, the wave shape, frequency, and sequence of instantaneous value changes in the second output signal can be varied.

In addition, the control unit can select the instructions in the additional memory concerning the sequence in which the discrete values are transferred out of the second intermediate memory, so that the sequence of amplitude changes, the frequency, and the wave shape of the interference signal obtained by adding the first and second output signals together is controlled by the instructions selected by the control unit.

In still another embodiment, the chronological address allocation unit comprises means for varying the period of at least one of the output signals. Furthermore, the means for varying the period of at least one of the output signals can comprise a counter for addressing the first and second intermediate memories, a frequency divider, and an adder, in such a manner that the frequency divider and the adder control the counter.

In still another embodiment, at least one of the intermediate memories comprises a read/write memory. In still another embodiment, both of the intermediate memories comprise read/write memories. In addition, these read/write memories can comprise a random access memory. In addition, the device can further comprise means for controlling the wave shape of the first and second output signals.

In another embodiment, the invention comprises a method of providing a first output signal whose instantaneous value varies with time at the output of an electrostimulation therapy device. The first signal has first a desired sequence of instantaneous value changes and a first desired wave shape and frequency. The method comprises of steps of selecting a first desired sequence of instantaneous value changes and a first desired wave shape and frequency of the first output signal with an adjustable control unit; storing predetermined data in a program memory, wherein the data comprises a plurality of discrete values representing the first output signal which has a predetermined instantaneous value variations with time, and wherein each discrete value represents a particular amplitude of the first output signal at a particular time; selecting data from the program memory in a first predetermined sequence to produce a first plurality of discrete values in a first predetermined sequence corresponding to the first desired sequence of instantaneous value changes selected with the adjustable control unit; transferring the first plurality of discrete values in the first predetermined sequence to a first intermediate memory; retrieving the first plurality of discrete values in the first predetermined sequence at a first predetermined speed to produce a first output signal having the first desired sequence of instantaneous value changes and the first desired wave shape and frequency; converting this first output signal to a first analog output signal; and applying the first analog output signal to the exterior of the body through electrodes.

The method further comprises selecting a second desired sequence of instantaneous value changes and a second desired wave shape and frequency of a second output signal with an adjustable control unit; selecting data from the program memory in a second predetermined sequence to produce a second plurality of discrete values in a second predetermined sequence corresponding to a second desired sequence of instantaneous value changes selected with the adjustable control unit; transferring the second plurality of discrete values in the second predetermined sequence to a second intermediate memory; retrieving the second plurality of discrete values in a predetermined sequence at a second predetermined speed to produce a second output signal having the second desired sequence of instantaneous value changes and the second desired wave shape and frequency; converting the second output signal to a second analog output signal; and applying this second analog output signal to the exterior of the human body through electrodes.

The method can further comprise adding the two output signals together. In addition, the method can be further comprise selecting the first and second predetermined speeds for retrieving the first and second plurality of discrete values such that beats are produced when the two output signals are added together.

Furthermore, the retrieving step for retrieving the second plurality of discrete values can further comprise, in one embodiment, retrieving the second plurality of discrete values in the second predetermined sequence. In an alternative embodiment, this retrieving step can comprise, alternatively, the step of retrieving the second plurality of discrete values in a third predetermined sequence, different from the second predetermined sequence, before the second plurality of discrete values are added to the first plurality of discrete values.

According to another embodiment of the invention, the invention is directed to a device for electrostimulation therapy of the cited type, in which a microprocessor is provided as a central control and processing unit for the production of the desired curve shapes and frequencies on the basis of information and instructions from program memory, and an input and control unit. The microprocessor is attached to at least one intermediate memory in which are stored the curves and frequencies in the state of transient or discrete values. A frequency divider and a unit for chronological address allocation is provided, which permit a reading out of the transient values of the curve stored intermediately in intermediate memory on the basis of information demanded through the microprocessor to plot the curves. In one preferred configuration, the unit for chronological address allocation has at least one counter controlled by a pulse oscillator or a divider.

For use specifically in electrical interference therapy, in which the device is equipped with at least two separate circuits and associated amplifiers, one preferred embodiment of the device is provided, according to the invention, in which to each circuits is connected an intermediate memory for intermediate storage of the transient values for the curves of the output voltages.

As opposed to the present state of the art, according to the invention, there is carried out neither a dividing down, particularly with electrical frequency therapy, through different divider ratios, of a high starting frequency to the desired frequency or frequencies, nor is there undertaken an analog storage of the most varied curves which are used.

With the device according to the invention, the desired curves and treatment procedures are formed instead on the basis of a few output data and programs, which are present in perse known memories, in which a relatively limited storage capacity suffices, and are stored in an intermediate memory in the form of transient values of the curves to be given out and are read from these in pulses which can be set, i.e., in controllable pulses. Therefore, the transient values of the curves are retrieved in the controllable pulse in a manner such that the oscillation frequency and curve appear at the output, i.e., the electrodes laid on the body to be treated have the required curve and frequency and, in the case of electrical interference treatment, the electrodes have the required curves and frequencies, and the required curve and frequency of the beats will arise inside the body by means of linear addition of the transient values of both output curves.

Addresses are formed by means of the pulse frequency produced from the oscillator, which has an oscillating quartz in advantageous configuration, and by means of the control signals produced in the frequency divider, which can be influenced, i.e., controlled, according to the predetermined values in the divider. These addresses are formed by means of the device according to the invention, by which the corresponding instantaneous values are extracted for formation of the curve. The problems and disadvantages of the known devices are overcome by the device according to the invention, and particularly, a great multiplicity and freedom of therapy in the field of electrostimulation therapy, and above all, in electrical interference therapy, is attained at low cost.

One essential advantage of the device according to the invention lies in that, e.g. with interference current, the lower limit for the oscillation frequency can be made as small as desired. Basically, the lower limit for the oscillation frequency can be selected as desired. The number of instantaneous values for different curves of different electrostimulation therapies is basically determined by the required degree of faithfulness of the curve produced of the output signal to its ideal form and in case of interference current therapy of the curve itself and the degree of faithfulness of the curve to the desired beat curve. Advantageously, one proceeds in such a manner that the number of instantaneous values will not be determined simultaneously through all of these quantities, but rather merely through the cited quantity, which is sought with the greatest precision and which therefore requires the highest number of discrete values or supports for the initial curve.

The invention particularly provides that, on the one hand, any desired shape of the output curve, and therefore in case the electrical interference therapy, any desired beat curve shape, can be produced, while the allocation of the instantaneous values is controlled in correspondence with the desired curve. Very many different instantaneous values for one period can therefore be intermediately stored by simple means, and simultaneously, a plurality of different curves can be attained, including both as output curves and also, with electrical interference, the beat curves, which with known devices would have required either a very expensive electronic frequency-divider or else an exceedingly large storage capacity. With non-sinusoidal curves, such as, e.g., a triangular or peak like beat or interference curve, known devices require additional technically very demanding nonlinear control devices.

A frequency divider is provided according to one preferred configuration of the invention, regulated by the quartz oscillator, which can be freed from the microprocessor, so that a different number of supports or instantaneous values can be attained over a period. According to another preferred configuration of the invention, the chronological address allocation unit has a counter controlled by the oscillator and frequency divider and especially has a further counter controlled by the oscillator and frequency divider and an adder. First, the instantaneous values stored in the intermediate memories are time-controlled retrieved by the counter controlled by the oscillator and frequency divider. Variations of the stored curves and, with interference current particularly, shifts of both curves in opposition to one another, and thus the oscillations, but above all variable beats, can be attained by means of the other counter and the adder. According to another preferred configuration, the chronological address allocation unit has another, freely flexible programmable memory. The stored curves are reproduced by storage of a linear function in electrical interference, while with storage of a nonlinear function, a nonlinear shift of one of the two curves can be attained with interference current and also therewith a change of the shape of the beat curves in deviation from the output shapes.

BRIEF DESCRIPTION OF THE DRAWINGS

The above and other objects, features and advantages of the present invention arise from the claims and from the following detailed description, wherein one embodiment of the invention is explained for electrical interference therapy relative to the drawings wherein:

DETAILED DESCRIPTION OF PREFERRED EMBODIMENTS

Figure 1:
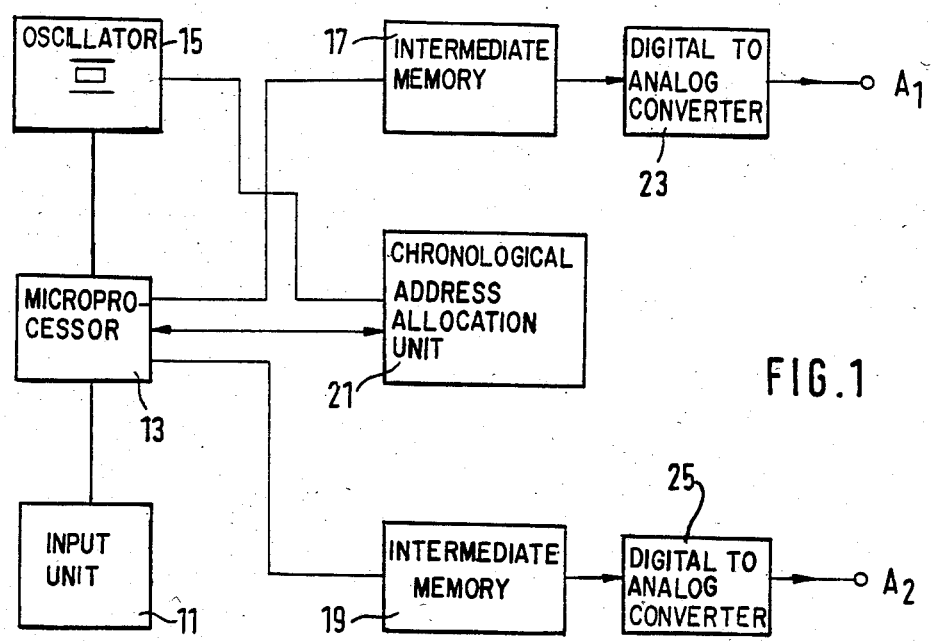
FIG. 1 is a block diagram of the embodiment of the device according to the invention for electrical interference therapy.

The diagram of FIG. 1 shows the device according to the invention with an input unit 11. Pulse generator or oscillator 15 is also provided, which produces the separate pulse frequencies.

The key elements of the device according to the invention in the embodiment shown for electrical interference therapy are first of all two intermediate memories 17 and 19 for specific curves. If no electrical interference therapy, but rather only an electrostimulation therapy, with one pair of electrodes, is carried out, then, of course, only one such intermediate memory is necessary.

A unit for chronological address allocation 21 is provided for the control of intermediate memories 17, 19 or for the retrieval of curves stored therein, or more precisely, for retrieval of their transient or discrete values, which is controlled by microprocessor 13 taking into account a pulse produced by pulse generator 15.

Digital-to-analog-converters 23, 25 are respectively series-connected to intermediate memories 17, 19 which convert the instantaneous values stored digitally in the intermediate memories into an analog signal. The analog signal can then be amplified by an amplifier (not shown) and is then passed for treatment to the relevant pair of electrodes (also not shown).

Figure 2:
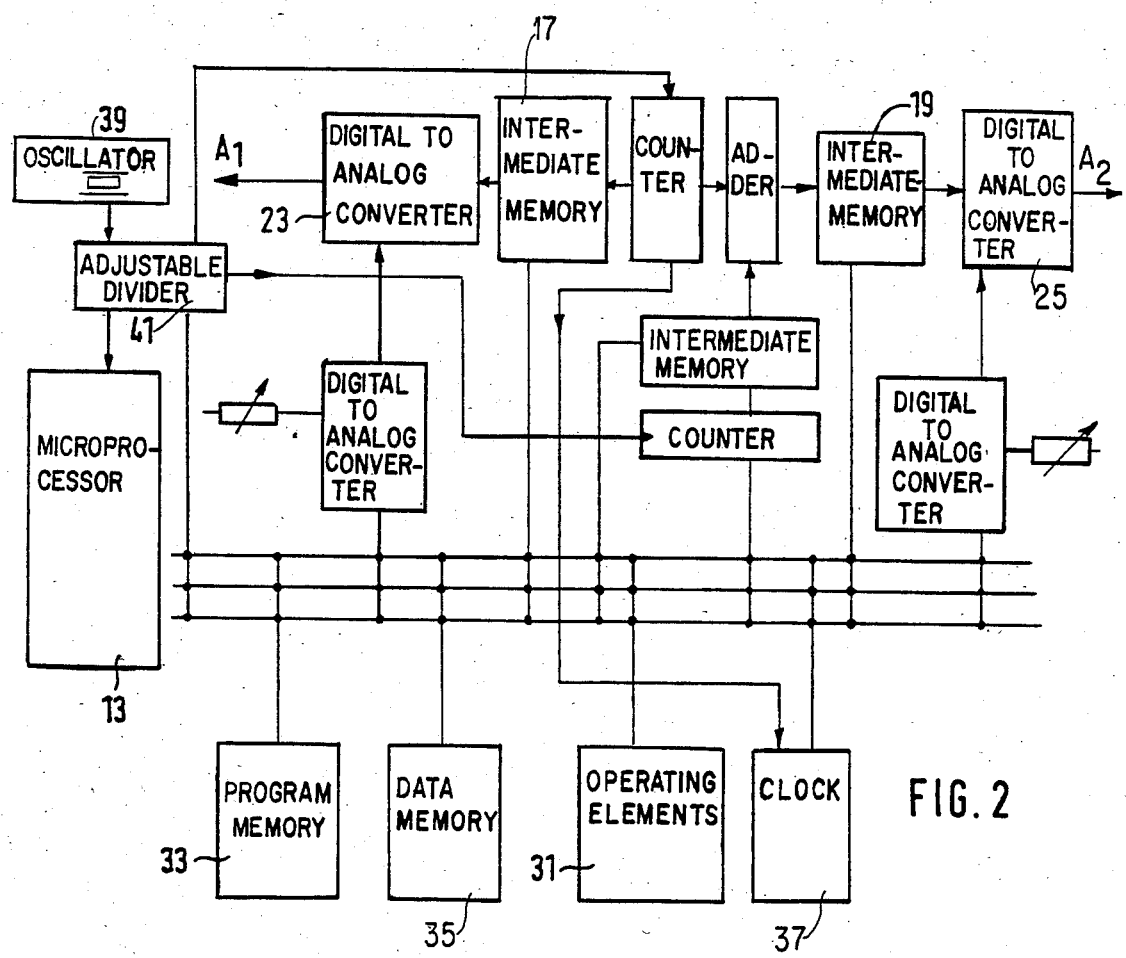
FIG. 2 is a detailed circuit diagram, also for use in electrical interference therapy.

It is shown in FIG. 2 that the input unit 11 in the embodiment shown includes operating elements 31, a program memory 33 and a data memory 35. Data or program elements as well as algorithms are stored in these memories, on the basis of which the desired curves can be produced as desired by the therapist through the operating elements with the microprocessor digital representations, as will be discussed below with reference to FIG. 4. The intermediate memories 17, 19, which can be RAM's, i.e., Random Access Memories, i.e., a memory with direct access, which can especially be write/read memories, are used to store these digital representations intermediately. The digital representations are retrieved from the intermediate memories 17, 19 in a controlled manner by the chronological address allocation unit 21.

Figure 4:
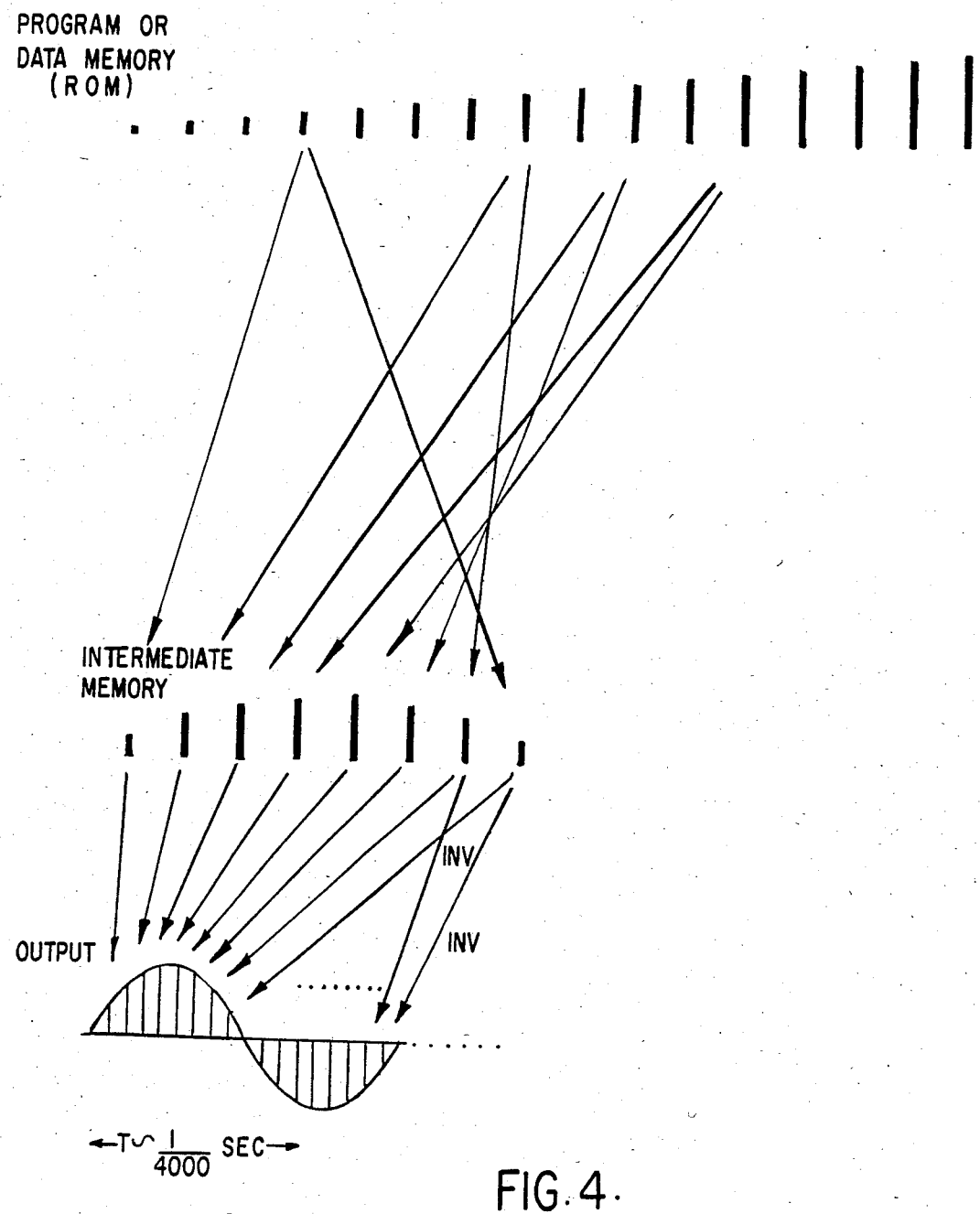
FIG. 4 is a schematic view of the transfer of data from the program to the intermediate memory, and from the intermediate memory to the electrodes.

FIG. 4 illustrates the manner in which the output signal is produced from the program memory. As can be seen in FIG. 4, the program memory can be in the form of a ROM, which stores data in the form of different discrete values, which represent the instantaneous value at a particular time of the output signal. The microprocessor selects data having various values from program memory in a predetermined sequence so as to produce plurality of discrete values is a predetermined sequence corresponding to the desired sequence of instantaneous value changes chosen by the user with the adjustable control unit. The microprocessor then transfers these discrete values to the intermediate memory in this predetermined sequence as is also seen in FIG. 4.

The address means, which is responsive to the microprocessor, then transfers these discrete values stored in the intermediate memory to the digital-to-analog converter in this predetermined sequence, and at a predetermined speed, so as to produce the output signal having the desired sequence of instantaneous value changes in the desired wave shape and frequency that is selected by the user with the adjustable control unit, as seen at the bottom of page 4. In this manner, an output signal of any shape can be easily produced using a minimum of circuitry.

In another embodiment, two separate output signals are produced in the identical manner to the output signal discussed above and shown in FIG. 4. In this embodiment, two intermediate memories are provided, each for receiving and storing either the same or different sequences of discrete values in each intermediate memory. In addition, in still another embodiment, the sequence of instantaneous value changes in the one of the intermediate memories can be changed as the address means transfers these discrete values out of one of the intermediate memories, as will be discussed below. In this way, the shape of the interference signal that is produced by adding the two output signals together from the two intermediate memories can be varied in any manner chosen by the user.

A clock 37, by which the length of treatment can be controlled in a known manner, is also included in the input unit.

The pulse generator 15 has a quartz oscillator 39, as a pulse oscillator, and also a frequency divider 41.

In FIG. 2, intermediate memory 17 or 19 is indicated for clarity as SP1 for the curve 1 or the output 1A1 and as SP2 for the curve 2 or the output 2A2. Particularly, the central unit of the invention for the chronological address allocation of an electrical interference therapy device is respresented in more detail in FIG. 2.

Figure 3:
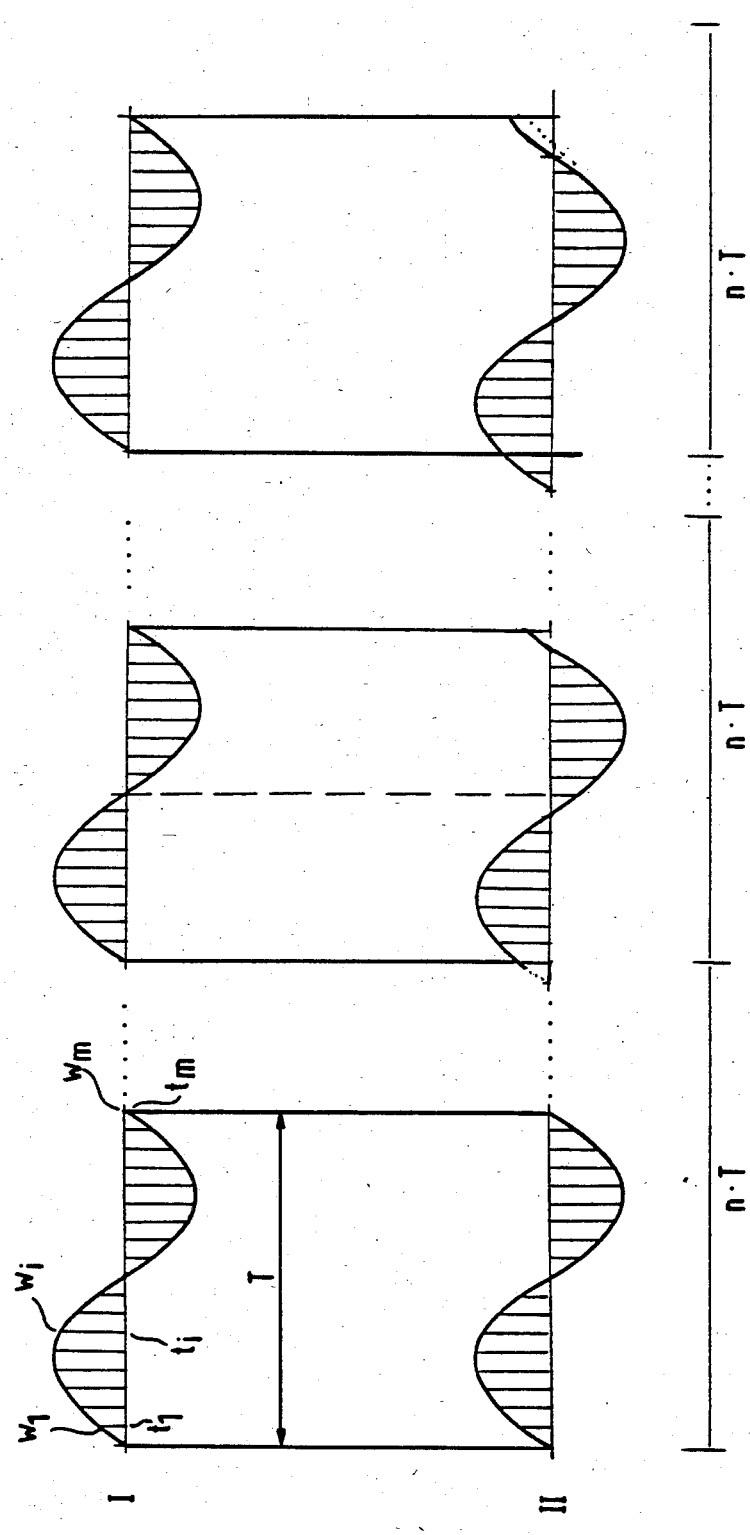
FIG. 3 is a representation of the chronological allocation of the instantaneous values of two output curves retrieved from intermediate memory for electrical interference therapy.

Counter Z1 is first controlled from the quartz oscillator 39 through adjustable device 41. The counter Z1 in turn retrieves by means of counting the desired different instantaneous values from memory SP1 counting whereby the desired curve is produced; further the counter Z1 feeds the transient values through the digital-to-analog-converter 23 to the output A1 and thus to the relevant pair of electrodes. The analog-produced curve in FIG. 3 for the form of a sinusoidal curve is shown next to the number 1 for three oscillations at different time points. Therein, T means an oscillation time of curve I, i.e., for example, the voltage at the first pair of electrodes.

The counter Z1 at time point $t_1$, for example, reads the relevant digital value for the instantaneous voltage value $w_1$ (FIG. 3) from the memory SP1, and this digital value is then converted into the analog voltage value $w_1$. With counting through, in a corresponding manner, at times $t_i$ the associated voltage values $w_i$ are produced, until the counter arrives at its final value $t_m$ and at its associated voltage value $w_m$, which here is equal to zero. The counter is then set back and the counting process begins once again with the reading of the separate voltage values.

The counter Z1 is also connected with the clock 37.

Furthermore, counter Z1 is connected through an adder $\Sigma$ with intermediate memory SP2. If the adder $\Sigma$ is not to be used for addition, then the curve stored therein is retrieved from memory SP2 in the same manner as the curve stored in memory SP1. Particularly with both memories, after the running down of the counter, the registration is begun again from the beginning with the same time period.

Another counter ZII is to be used particularly in order to be able to produce another period in memory SP2 and therewith to be able to allocate another frequency to curve 2, from divider 41, which can be set by microprocessor 13. Free and flexible adjustable memory contents from memory SP3 are fed through counter ZII to adder $\Sigma$, whereby a variation can be produced in the reading of memory SP2 for the second curve. For example, a repetition of the oscillation curve is attained with storage of a linear function in memory SP3. In order to obtain a change of the oscillation shape, a nonlinear shift of the second curve can be placed in memory SP3, from which the change of oscillation shape results throughout the treatment time.

The following now is attained by means of the device according to the invention in the embodiment shown: by means of a selected switching of operational elements 31, instantaneous values of two similar or dissimilar curves are formed in microprocessor 13 by means of data called from program memory 33 and data memory 35. Then, by means of a quartz-stabilized oscillator 39 and divider 41, such instantaneous values are called in synchronization from each memory Sp1 and Sp2 by means of a pulse produced by quartz-stabilized oscillator 39 and divider 41, which create at the outputs A1 and A2 the required curve shape, frequency and—when the instantaneous values of the two arising curves are added algebraically—the required interference oscillation or beats with the corresponding beat frequency and shape of curve. This way the hardware according to the invention is initialized by means of microprocessor 13 on the basis of predetermined data stored in program memory 33 and data memory 35 or software—which is not included in the disclosure of the invention—so that the required curve shapes arise at outputs A1 and A2.

With the cited pulse frequencies, which are generated by oscillator 39 and divider 41, by counter ZII addresses are called in the device according to the invention, among which are found the suitable instantaneous values for the curve formation.

E.g., the desired shape of the interference curve as a relation between count number and address will be intermediately stored in memory Sp3 as instantaneous values $w_1, w_2, \ldots w_i \ldots w_n$ under its addresses 1, 2, .. i, ... n. Now if for example the value of a sine-curve are stored in memories Sp1 and Sp2, the interference curve is as well a sine-curve. If one wishes a sine-curve as interference curve the respective relation is given to memory Sp3; the relation can simply be that if counter ZII has its counter number "i" the address "i" will be called from memory Sp2 and the instantaneous value $w_i$ given as output. The counter ZII itself is set (and reset when the reaches its given maximum value) by the pulses of the oscillator 39 eventually divided by divider 41. But if another shape of interference curve is desired the relation can be another one for example such that with count number "i" the address "j" is called and accordingly value $w_j$ is given out. The relation "i−j" is determined by the shape fo the interference curve requested and as code stored in memory Sp3.

If one assumes that curve I should present the same shape throughout the entire treatment time, this is attained by calling the instantaneous values associated with the required curve shape periodically from memory Sp1 at T time intervals. The instantaneous values after a time period n×T, which is determined essentially by counter ZII and memory SP3, are newly allocated by curve II and are periodically repeated during the next time period n (or even another n') ×T with this new allocation. In this manner an interference beat curve, of which the frequency is dependent on n, arises, wherein n is the number of periods of the medium frequency curve after which occurs a new allocation of the instantaneous values of curve II. Since n can be chosen as desired and particularly can be as large as desired, any even very small interference frequency is possible. Any desired beat or interference curve can be produced, and the allocation of the instantaneous value of curves I and II, which is also as desired, is selected corresponding to the required curve shape.

Therefore, good stabilization of the oscillation frequency is attained according to the invention. Interference frequency or beat frequency of the beat curve is equal to the difference of the output frequencies. The interference or beat curve is the envelope of a high or medium frequency oscillations with a frequency the arithmetic mean of the output frequencies. Furthermore, the cost of the memory for solid state storage is held low, and still, a plurality of different curves, such as sinusoidal, rectangular output signals or even sinusoidal, rectangular and even triangular oscillations can be attained with or without pauses.

In the above description, in the drawings as well as in the claims, the features of the invention can be either separate or essentially in any desired combinations for the implementation of the invention in its various embodiments.

From the foregoing description, one skilled in the art can easily ascertain the essential characteristics of the invention and, without departing from the spirit and scope thereof, can make various changes and modification of the invention to adapt it to various usages and conditions.

What is claimed is:

1. A device for electrostimulation therapy for producing an output signal having a desired sequence of instantaneous value changes and a desired waveshape and frequency to stimulate a portion of the human body, wherein said device comprises:

(a) a program memory for storing data comprising a plurality of discrete different values representative of signals having predetermined instantaneous value variations with time, wherein each discrete value comprises a particular instantaneous value of said signal at particular time;

(b) an adjustable control unit for selecting a desired sequence of instantaneous value changes and a desired waveshape and a desired frequency of said output signal;

(c) an intermediate memory for receiving and storing data from said program memory;

(d) a microprocessor responsive to said control unit for selecting said data in a predetermined sequence from said program memory so as to produce a plurality of discrete values in a predetermined sequence corresponding to said desired sequence of instantaneous value changes and for transferring said discrete values to said intermediate memory in said predetermined sequence;

(e) a digital to analog converter;

(f) at least one electrode connected to the output of said converter for engaging the exterior of said body and through which said output signal is transferred to said body; and (g) address means responsive to said microprocessor for transferring said discrete values stored in said intermediate memory to said digital to analog converter in said predetermined sequence and at a predetermined speed so as to produce said output signal having the desired sequence of instantaneous value changes and the desired waveshape and frequency selected by said adjustable control unit.

2. The device defined by claim 1 wherein said device further comprises: a pair of electrodes connected to said converter for engaging the exterior of said body; and an amplifier for amplifying said output signal before said output signal reaches said pair of electrodes.

3. The device defined by claim 2 further comprising an oscillator for controlling said the speed with which said address means transfers said discrete values from said intermediate memory to said digital to analog converter.

4. The device defined by claim 3 further comprising a frequency divider, wherein said address means comprises a chronological address allocation unit, wherein said oscillator is connected to said frequency divider and wherein said unit is controlled by said oscillator and said frequency divider.

5. The device defined by claim 4 wherein said chronological address allocation unit comprises memory means for storing a function relating to the varying of the waveshape of said output signal, wherein said chronological address allocation means varies the waveshape of said output signal in accordance with said function stored in said memory means.

6. The device defined by claim 5 wherein said function is a non-linear function, wherein said chronological address allocation unit varies the waveshape of said output signal in a non-linear manner in accordance with said non-linear function.

7. The device defined by claim 5 wherein said memory means is a programmable memory.

8. The device defined by claim 4 wherein unit comprises at least one counter controlled by said oscillator.

9. The device defined by claim 1 wherein said device is adapted to produce first and second output signals, each having a desired waveshape, frequency and sequence of instantaneous value changes, wherein said device further comprises first and second electrodes and first and second digital to analog converters, wherein said first electrode is connected to the output of said first digital to analog converter and said second electrode is connected to the output of said second digital to analog converter, wherein each electrode engages the exterior of said body, wherein said first output signal is transmitted to said body through said first electrode and said second output signal is transmitted to said body through said second electrode, wherein said intermediate memory comprises:

(i) a first intermediate memory for receiving and storing data from said program memory; and (ii) a second intermediate memory for receiving and storing data from said program memory, wherein said control unit selects a desired sequence of instantaneous value changes and a desired waveshape and frequency for each output signal, wherein said microprocessor selects discrete values in a predetermined sequence from said program memory so as to produce a first set of data comprising a plurality of discrete values in a predetermined sequence corresponding to the desired sequence of instantaneous value changes for said first output signal, and wherein said microprocessor selects discrete values in a predetermined sequence from said program memory so as to produce a second set of data comprising a plurality of discrete values in a predetermined sequence corresponding to the desired sequence of instantaneous value changes for said second output signal, wherein said microprocessor transfers said first set of data in said predetermined sequence to said first intermediate memory, and transfers said second set of data in said predetermined sequence to said second intermediate memory, wherein said address means transfers said first set of data from said first intermediate memory to said first digital to analog converter and transfers said second set of data from said second intermediate memory to said second digital to analog converter, whereby said device comprises means for performing electrical interference therapy on said body.

10. The device defined by claim 9 wherein said address means comprises means for transferring said first set of data from said first intermediate memory at a first speed to produce said first output signal, wherein said address means further comprises means for transferring said second set of data from said second intermediate memory at a second speed to produce said second output signal, wherein the frequency of said first output signal is different from the frequency of said second output signal.

11. The device defined by claim 10 wherein the frequency of said two output signals produced by said address means are sufficiently close together that beats are produced.

12. The device defined by claim 11 further comprising an additional memory for storing instructions for the sequence in which said discrete values are transferred from said second intermediate memory by said address means and the frequency of the second output signal produced from said discrete values in said second intermediate memory, wherein said address means transfers said second set of data out of said second intermediate memory in accordance with said instructions in said additional memory.

13. The device defined by claim 12 wherein said address means changes the sequence of discrete values in said second set of data stored in said second intermediate memory as said address means transfers said second set of data out of said second intermediate memory in accordance with instructions stored in said additional memory.

14. The device defined by claim 13 wherein said control unit selects said instructions in said additional memory concerning the sequence in which said discrete values are transferred out of said second intermediate memory, whereby the sequence of instantaneous value changes, the frequency and the waveshape of the interference signal obtained by adding said first and second output signals together is controlled by said instructions selected by said control unit.

15. The device defined by claim 9 wherein said chronological address allocation unit comprises means for varying the period of at least one of said output signals.

16. The device defined by claim 15 wherein said means for varying the period of at least one of said output signals comprises a counter for addressing said first and second intermediate memories, a frequency divider and an adder, wherein said frequency divider and said adder control said counter.

17. The device defined by claim 9 wherein at least one of said intermediate memories comprises a read/write memory.

18. The device defined by claim 9 wherein both of said intermediate memories are read/write memories.

19. The device defined by claim 18 wherein said read/write memories comprise a random access memory.

20. The device defined by claim 9 further comprising means for controlling the waveshape of said first and second output signals.

21. A method of providing a first output signal whose amplitude varies with time at the output of an electrostimulation therapy device, wherein said first signals has a first desired sequence of amplitude changes and a first desired waveshape and frequency, wherein said method comprises the steps of:

(a) selecting a first desired sequence of amplitude changes and a first desired waveshape and frequency of said output signal with an adjustable control unit;

(b) storing predetermined data in a program memory, wherein said data comprises a plurality of discrete values representing signals having predetermined instantaneous value variations with time, wherein each discrete value represents a particular instantaneous value of said signals at a particular time;

(c) selecting data from said program memory in a first predetermined sequence to produce a first plurality of discrete values in a first predetermined sequence corresponding to said first desired sequence of instantaneous value changes selected with said adjustable control unit;

(d) transferring said first plurality of discrete values in said first predetermined sequence to a first intermediate memory;

(e) retrieving said first plurality of discrete values in said first predetermined sequence at a first predetermined speed to produce a first output signal having said first desired sequence of amplitude changes and said first desired waveshape and frequency;

(f) converting said first output signal to a first analog output signal; and (g) applying said first analog output signal to the exterior of a human body through electrodes.

22. The method defined by claim 22 further comprising:

(h) selecting a second desired sequence of amplitude changes and a second desired waveshape and frequency of a second output signal with said adjustable control unit;

(i) selecting data from said program memory in a second predetermined sequence to produce a second plurality of discrete values in a second predetermined sequence corresponding to said second desired sequence of instantaneous value changes selected with said adjustable control unit;

(j) transferring said second plurality of discrete values in said second predetermined sequence to a second intermediate memory;

(k) retrieving said second plurality of discrete values in a predetermined sequence at a second predetermined speed to produce a second output signal having said second desired sequence of amplitude changes and said second desired waveshape and frequency;

(l) converting said second output signal to a second analog signal; and (m) applying said second analog signal to the exterior of said human body through said electrodes.

23. The method defined by claim 22 further comprising the step of:
(n) adding said two output signals together.

24. The method defined by claim 23 further comprising the step of:
(o) selecting said first and second predetermined speeds for retrieving said first and second plurality of discrete values such that beats are produced when said two output signals are added together.

25. The method defined by claim 24 wherein said retrieving step (k) further comprises the step of:
(p) retrieving said second plurality of discrete values in said second predetermined sequence.

26. The method defined by claim 24 wherein said retrieving step (k) further comprises the step of:
(q) retrieving said second plurality of discrete values in a third predetermined sequence, different from said second predetermined sequence before said second plurality of discrete values are added to said first plurality of discrete values.

* * * * *